US00PP24455P3

(12) United States Plant Patent
Villegas

(10) Patent No.: US PP24,455 P3
(45) Date of Patent: May 13, 2014

(54) ***SANSEVIERIA* PLANT NAMED 'KRISTI'**

(50) Latin Name: *Sansevieria trifasciata*
Varietal Denomination: Kristi

(75) Inventor: Marvin Gonzalez Villegas, San Ramon (CR)

(73) Assignee: Florica Farms, Inc., Eustis, FL (US)

( * ) Notice: Subject to any disclaimer, the term of this patent is extended or adjusted under 35 U.S.C. 154(b) by 0 days.

(21) Appl. No.: 13/374,901

(22) Filed: Jan. 23, 2012

(65) Prior Publication Data

US 2013/0191951 P1 Jul. 25, 2013

(51) Int. Cl.
*A01H 5/00* (2006.01)

(52) U.S. Cl.
USPC ..... Plt./382

(58) Field of Classification Search
USPC ..... Plt./382, 263.1, 226
See application file for complete search history.

*Primary Examiner* — Kent L Bell
(74) *Attorney, Agent, or Firm* — Foley & Lardner LLP

(57) ABSTRACT

The new variety 'Kristi' is part of the "compact *sansevieria* varieties". It can reach up to 55 cm in length, with an average of 5-6 leaves per plant. The plant is shaped like an inverted pyramid, the arrangement of the leaves is in the form of a rosette. Shows colors very similar to its parent variety 'Black Gold Superba'. However 'Kristi' shows semi twisted blades, moderate green coloration in the blade and horizontal lines on the upper surface of mature leaves. The margins are green-yellow with horizontal green-yellow stripes.

3 Drawing Sheets

Latin name of the genus and species of the claimed plant: *Sansevieria trifasciata.*

Variety denomination: 'Kristi'.

BACKGROUND OF THE INVENTION

The present invention relates to a new and distinct cultivar of *Sansevieria* plant, botanically known as *Sansevieria trifasciata*, of the family Ruscaceae, hereinafter referred to by the cultivar name 'Kristi'.

*Sansevieria* is a monocotyledonous and succulent, flowering plant which can be produced in either hard-leafed or soft-leafed varieties for interior use as a house plant or outdoor ornamental plant.

The new *Sansevieria* 'Kristi' was discovered and selected by Mr. Marvin Gonzalez Villegas, as a single flowering plant within a planting of 'Black Gold Superba' at Monterrey, San Carlos, Alajuela province, Costa Rica in 2004. It originated as a naturally-occurring mutation of the *Sansevieria* variety 'Black Gold Superba' (unpatented).

Asexual reproduction of the new *Sansevieria* cultivar by vegetative cuttings was first performed in November 2005 in Monterrey, San Carlos, Alajuela, Costa Rica and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'Kristi', which in combination distinguish this *Sansevieria* as a new and distinct cultivar:

1. Moderate green foliage with pale yellowish green middle stripes and brilliant green yellow margins in the upper surface. Dark yellowish green blade with light greenish yellow margins in the lower surface.
2. 35 cm long, wide and lanceolate leaves supported in a rosette.
3. 25-55 cm plant height.
4. Erect Plant habit.
5. Needs little water and is moderately drought tolerant.

The claimed variety 'Kristi' is considered a variety of *Sansevieria* in the group denominated as "compact *Sansevieria* plants". The claimed variety presents between 5 and 6 leaves per plant when it reaches maturity (between 7-8 months). It has erect growth and the entire plant can reach a height range between 25-55 cm. The leaves are narrow (4.5 cm average measured at the widest part of the mature leaf) and lanceolate with a soft, waxy texture, and the blades are thin and slightly wavy. The plant has an inverted triangle shape.

The claimed variety is moderately drought tolerant, and adapts well to conditions of light and shade (interior and exterior).

The leaf blade is variegated, showing green color on the surface (RHS 135B and 139A), with non-uniform vertical lines in the center of the upper side of some leaves (RHS 149D). In addition, the leaves present 1.5 cm variegated margins on both sides which alternate in irregular horizontal bands of green-yellow (RHS 3D and RHS 2A).

Plants of the new *Sansevieria* 'Kristi' differ from plants of the parental cultivar, 'Black Gold Superba' (unpatented) in the characteristics described in Table 1.

The variety 'Black Gold Superba' gave rise to the var. 'Kristi'. The 'Black Gold Superba' variety is also considered to be part of the "compact *Sansevieria*" group. 'Black Gold Superba' shows less vigor than 'Kristi', less number of leaves per plant (3-4), with an average width of 6.5 cm (measured in the middle of the mature leaf). The growth habit is erect and presents wide leaves supported in a rosette. The entire plant can reach a size between 30-40 cm, and the plant has, as for 'Kristi', an inverted triangle shape. The leaves are lanceolate with a soft, waxy texture. The younger leaves show a green vivid coloration (RHS 134A) in the interior of the leaf blade. This area shows also irregular streaks or yellowish-green bands (RHS 142D) and the margins in both sides of the leaf are variegated with irregular horizontal bands that alternate with light yellowish green (RHS142D) broad bands and brilliant yellowish green (RHS 149A) thin bands. When the leaf is mature the deep color inside turns yellowish green (RHS 141B), while margins alternate vivid green-yellow (RHS 2A) and light-yellowish green (RHS 2C) colors.

TABLE 1

Comparison with Parental Variety

| Characteristic | New Cultivar 'Kristi' | Female Parent 'Black Gold Superba' (unpatented) |
|---|---|---|
| Plant Vigor | more vigorous (more leaves) | less vigorous (less leaves) |
| Color | Moderate green foliage with pale yellowish green middle stripes and brilliant green-yellow margins in the upper surface. Dark yellowish green blade with light green-yellow margins in the lower surface. | green leaves with yellow margins. |
| Shape | wide and lanceolate leaves on a rosette | wide and lanceolate leaves |
| Texture of leaves | smooth-textured leaves | smooth-textured leaves |

Of the many commercial cultivars known to the present inventor, the most similar in comparison to the new *Sansevieria* 'Kristi' is the *Sansevieria* 'Black Gold Superba' (unpatented), in the characteristics described above.

BRIEF DESCRIPTION OF THE PHOTOGRAPHS

The accompanying photographs illustrate the overall appearance of the new *Sansevieria* cultivar 'Kristi' showing the colors as true as is reasonably possible with colored reproductions of this type. Colors in the photographs may differ slightly from the color value cited in the detailed botanical description which accurately describe the color of 'Kristi'.

DETAILED BOTANICAL DESCRIPTION

Figure 1:
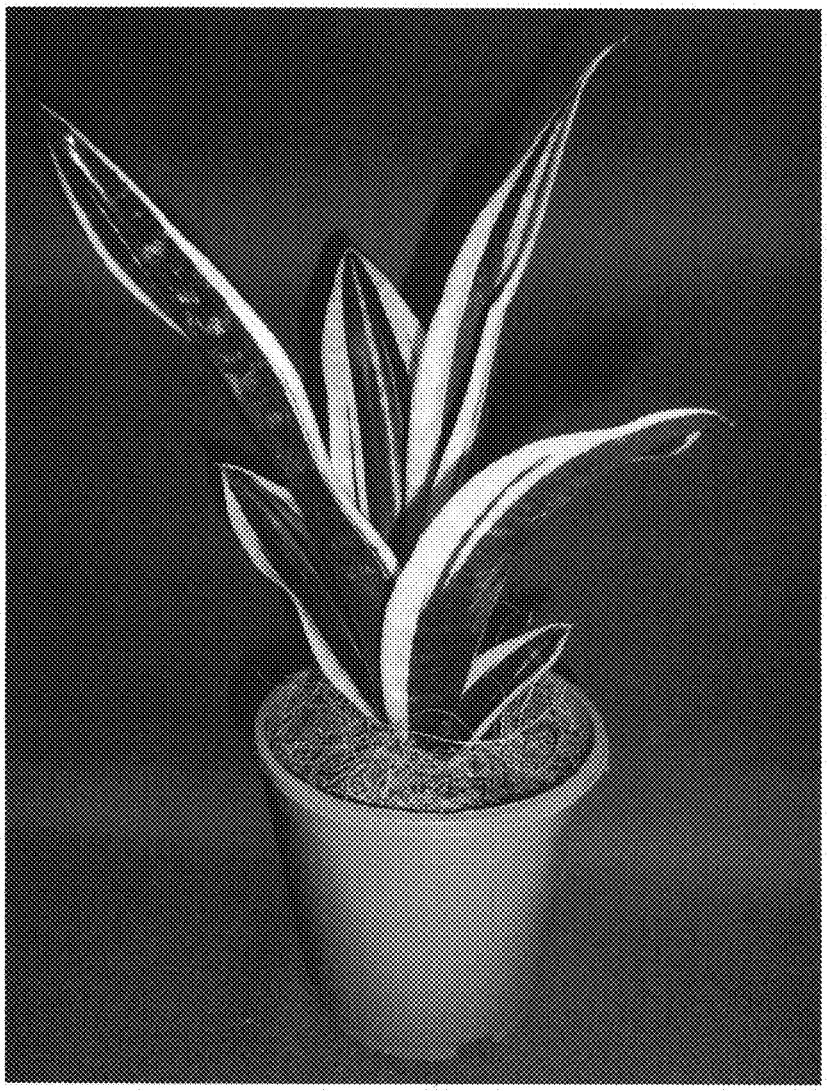
FIG. 1 Shows a side view of a seven-month old plant of *Sansevieria* 'KRISTI' in a 21 cm diameter pot.
Figure 2:
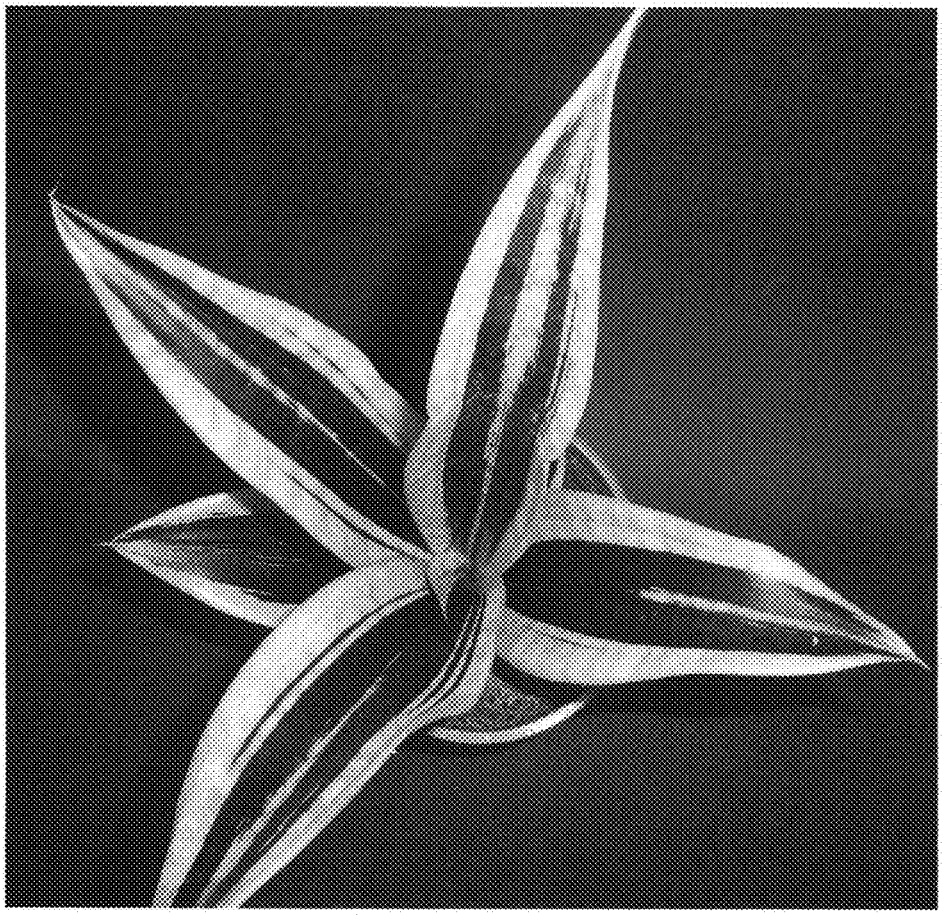
FIG. 2 Shows a top view of a seven-month old plant of *Sansevieria* 'KRISTI' in a 21 cm diameter pot.
Figure 3A:
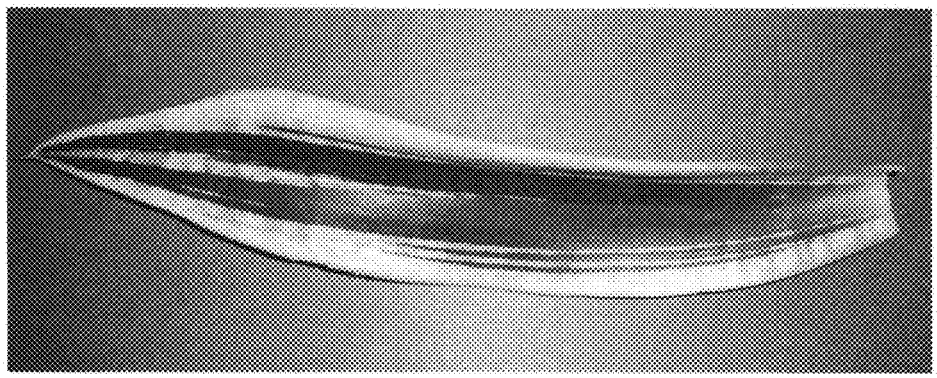
FIG. 3A Shows a close-up view of the upper side of a typical leaf of 'KRISTI', taken from an eight-month old plant.
Figure 3B:
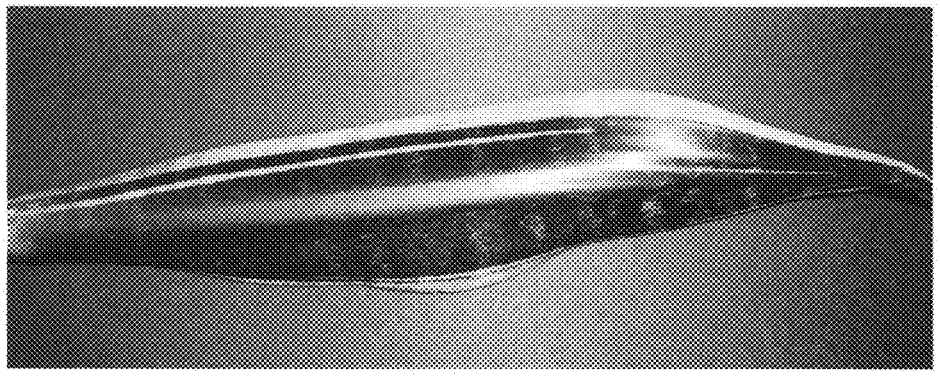
FIG. 3B Shows a close-up view of the lower side of a typical leaf of 'KRISTI', taken from an eight-month old plant.

The new *Sansevieria* 'Kristi' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Sansevieria* cultivar 'Kristi' as grown in an open field in Monterrey, San Carlos de Alajuela province, Costa Rica, under conditions which closely approximate those generally used in commercial practice. Average temperature in Monterrey is 24.5° C. during the day and 18° C. at night. Plants grow under natural light conditions.

This crop does not require constant fertilization, however, increasing production per area requires about 200 kg $ha^{-1}$ N, 150 kg $ha^{-1}$ of P and 100 kg $ha^{-1}$ K. The production is closely related with soil conditions in which the plants are grown.

Color references are made to The Royal Horticultural Society Color Chart (R.H.S., April 2009). The photographs and descriptions were taken during the rainy season in Monterrey, San Carlos, Alajuela province, Costa Rica when outdoor day temperatures ranged from 23° C. to 27° C. The age of the plants described is 8 months.

Classification:

*Botanical.*—*Sansevieria trifasciata.*

*Variety denomination.*—'Kristi'.

Parentage: *Sansevieria trifasciata* 'Black Gold Superba' (unpatented).

Optimal growth conditions:

*Light intensities.*—High adaptability to outdoor or indoor conditions.

*Temperature.*—Day: 24° C. to 32° C. Night: 18° C. to 23° C.

*Temperature tolerance.*—Tolerant to a low temperature of about 12° C. and tolerant to a high temperature of about 35° C.

*Fertilization.*—200, 150 and 100 kg $ha^{-1}$ of N, P and K.

*Growth regulators.*—None.

Propagation:

*Type.*—Vegetative, by rooted cuttings.

*Rooting habit and description.*—Rhizomes, with short roots.

*Time to initiate roots.*—About 15 to 22 days at 18-25° C.

*Time to produce a rooted cutting.*—About 60 to 90 days at 18-25° C.

Plant:

*General appearance and form.*—Height: between 22 and 55 cm when grown in ground and about 35 cm when grown in a 21 cm size container. Spread: About 14 cm when grown in ground; About 12 cm when grown in 21 cm size container. Form: Monocot; leaf bases arranged in a rosette around growth point. Shape: inverted triangle. Growth rate and habit: About 2 cm per week; upright. Fragrance: none. Stem: Modified (Rhizome and Foliage). Length: About 7 cm when grown in ground; About 5 cm when grown in 21 cm size container. Diameter: About 2 cm to 2.8 cm. Shape: round. Texture: rough. Color: RHS 17A. Strength: strong and durable. Internode length: About 0.3 mm to 0.7 mm.

Foliage:

*Quantity.*—Between 5 and 6.

*Arrangement and attachment.*—Single, alternate; leaf bases arranged in a rosette around growing point.

*Leaf length.*—About 28 cm.

*Leaf width.*—4.5 cm average.

*Overall shape of leaf.*—Lanceolate.

*Apex shape.*—Acute, triangular.

*Base shape.*—Plane.

*Margin.*—Sharp, smooth.

*Texture.*—Upper Surface: smooth and waxy. Under Surface: smooth and waxy.

*Pubescence.*—None.

*Color of mature leaf.*—Upper Surface: Moderate green blade RHS 135B, Pale Yellowish Green middle stripes: RHS 149D, Brilliant Green-Yellow margins RHS 3D and 2A. Lower Surface: Dark Yellowish Green blade RHS 139A, Light Green Yellow margins RHS 3D and 2A.

*Color of immature leaf.*—Upper Surface: RHS 139A, Center Stripes: RHS149D, Margins: RHS3D and RHS2A. Lower Surface: RHS 139A, Margins: RHS3D and RHS2A.

*Venation.*—Pattern: longitudinal/parallel leaf shape.

*Leaf fragrance.*—None.

Inflorescence description:

*Arrangement and type.*—Inflorescence.

*Orientation at opening.*—Out of the spike.

*Quantity per plant with at least one open flower.*—One inflorescence per plant. About 22 flowers opened 2 weeks after appearance of the spike. The plant flowers sporadically but profusely under growth conditions.

*Inflorescence size.*—Length: About 28 cm. Diameter: About 4.0 cm.

*Flower size.*—Length: About 2 cm. Diameter: About 1.0 cm. Depth: About 1.0 cm.

*Fragrance.*—Soft and pleasant.

*Bud.*—Rate of opening: About 7 to 8 days, according to weather. Shape: ovoid. Length: About 2.3 cm. Diameter: About 3.0 mm. Color: Apex: RHS 150A. Base: RHS 142A.

*Texture* (*both surfaces*).—Smooth.

Petals:

*Quantity.*—6.

*Arrangement.*—Star-shaped. No further data on the instant plant's petals was collected.

Reproductive organs:

*Androecium.*—Stamen: Number: 5 per flower. Length: About 1.3 cm. Color: RHS 150C. Anther: Length: About 0.2 mm. Width: About 0.1 mm. Color: RHS 150C. Filament: Length: About 1.1 mm. Color: RHS 150C. Pollen: Amount: moderate. Color: RHS 154D.

*Gynoecium.*—Pistil: Number: One per flower. Length: About 2.1 cm. Stigma: Length: About 0.6 mm. Width: About 0.8 mm. Color: RHS 150C. Style: Length: About 1.3 mm. Color: RHS 150C. Ovary: Length: About 3 mm. Width: About 2.5 mm. Color: RHS 150C.

Fruit: None observed.

Weather resistance: Drought tolerant.

Disease/pest resistance: Not observed for disease/pest resistance.

Disease/pest susceptibility: Not observed for disease/pest susceptibility.

I claim:

1. A new and distinct variety of *Sansevieria* plant named 'KRISTI', substantially as illustrated and described herein.

* * * * *